US005601826A

United States Patent [19]
Halpern

[11] Patent Number: 5,601,826
[45] Date of Patent: Feb. 11, 1997

[54] PEPTIDE WHICH PRODUCES PROTECTIVE IMMUNITY AGAINST TETANUS

[75] Inventor: Jane L. Halpern, Washington, D.C.

[73] Assignee: The United States of America as represented by the Department of Health and Human Services, Washington, D.C.

[21] Appl. No.: 231,437

[22] Filed: Apr. 20, 1994

Related U.S. Application Data

[63] Continuation of Ser. No. 906,841, Jun. 30, 1992, abandoned, which is a continuation-in-part of Ser. No. 373,862, Jun. 30, 1989, abandoned.

[51] Int. Cl.$^6$ .......................... A61K 39/08; A61K 38/10; C12N 7/08
[52] U.S. Cl. .................... 424/190.1; 424/193.1; 424/239.1; 514/13; 530/326; 930/200
[58] Field of Search ................ 424/190.1, 197.11, 424/239.1, 193.1; 530/326; 514/13; 930/200

[56] References Cited

U.S. PATENT DOCUMENTS

| 4,007,265 | 2/1977 | Helting | 424/239.1 |
| 4,479,940 | 10/1974 | Bizzini | 514/773 |
| 4,594,336 | 6/1986 | Bizzini | 514/2 |

FOREIGN PATENT DOCUMENTS

| 0209281A1 | 6/1986 | European Pat. Off. ........ C12N 15/00 |
| 0378881A1 | 12/1989 | European Pat. Off. .......... C07K 7/00 |
| 0430645A2 | 6/1991 | European Pat. Off. . |
| WO90/15871 | 12/1990 | WIPO . |

OTHER PUBLICATIONS

Andersen–Berkh et al, Infect. & Immun. 57(11):3498–3505. 1989.
Volk et al, Infect. & Immun. 45(3):604–609. 1984.
Sheppard et al, Infect & Immunity, 43(2):710–714, 1984.
Eisel et al, EMBO J., 5(10):2495–2502, 1986.
Simpson, J. Pharmacol. & Exp. Ther., 234(1):100–105, 1985.
Fattal et al, J. Biol Stand. 15:223–230, 1987.
Van Regenmortel, Phil Trons R Soc London, 323:454–466, 1984.
Makoff, et al., "Expression of Tetanus Toxin Fragment C in *E. Coli*: Its Purification and Potential Use as a Vaccine," *Bio/Technology*, vol. 7 (Oct. 1989), pp. 1043–1046.
Fairweather, et al., "Immunization of Mice against Tetanus with Fragments of Tetanus Toxin Synthesized in *Escherichia coli*" *Infection and Immunity*, vol. 55, No. 11 (Nov. 1987), pp. 2541–2545.
Fairweather, et al., "Cloning, Nucleotide Sequencing, and Expression of Tetanus Toxin Fragment C in *Escherichia coli*," Journal of Bacteriology, vol. 165, No. 1 (Jan. 1986), pp. 21–27.
Fairweather and Lyness, "The complete nucleotide sequence of tetanus toxin," *Nucleic Acids Research*, vol. 14, No. 19 (1986), pp. 7809–7812.
Halpern, et al., "Cloning and Expression of Functional Fragment C of Tetanus Toxin," *Infection and Immunity*, vol. 58, No. 44 (Apr. 1990), pp. 1004–1009.
Kenimer, et al., "Monoclonal Antibodies as Probes of Tetanus Toxin Structure and Function," *Infection and Immunity*, vol. 42, No. 3 (Dec. 1983), pp. 942–948.
Stibitz, Scott, et al., "Cloning and expression of DNA encoding tetanus–toxin fragment C'," *Chemical Abstracts*, vol. 113, Columbus, Ohio, U.S.

*Primary Examiner*—Mary E. Mosher
*Attorney, Agent, or Firm*—Townsend and Townsend and Crew

[57] ABSTRACT

The invention provides an immunogen against tetanus toxin including a peptide having a single, linear, antigenic, tetanus-toxin-specific epitope. The epitope is derived from the heavy chain C fragment of the toxin. In a preferred embodiment, the immunogen includes the last 20 amino acids of the toxin, including the carboxy terminus. Antibodies, including antipeptide antibodies, are also provided as well as methods of vaccination.

9 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Asp  Lys  Ile  Leu  Gly  Cys  Asp  Trp  Tyr  Phe  Val  Pro  Thr  Asp  Glu  Gly
1                  5                                  10                                 15
Trp  Thr  Asn  Asp
               20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
Cys  Asp  Lys  Ile  Leu  Gly  Cys  Asp  Trp  Tyr  Phe  Val  Pro  Thr  Asp  Glu
 1                   5                        10                            15

Gly  Trp  Thr  Asn  Asp
                    20
```

PEPTIDE WHICH PRODUCES PROTECTIVE IMMUNITY AGAINST TETANUS

This application is a File Wrapper Continuation of application Ser. No. 07/906,841, filed Jun. 30, 1992, abandoned Apr. 20, 1994, which was a Continuation-in-Part of application Ser. No. 07/373,862, filed Jun. 30, 1989, abandoned Mar. 16, 1994.

BACKGROUND OF THE INVENTION

Tetanus is an acute infectious disease caused by the anaerobic bacteria *Clostridium tetani*. A potent protein neurotoxin elaborated by the bacteria causes the manifestations of the disease. Typically, tetanus is characterized by neurological symptoms including convulsions and intermittent muscle spasms. Lockjaw is a common name for the disease. The neurotoxin inhibits neurotransmitter release by an undetermined mechanism of action believed to require at least three steps: 1) binding to a eukaryotic cell receptor, 2) translocation to the cytosol and 3) disruption of the secretory pathway.

The precise structure of the receptor for tetanus toxin has not been identified. Tetanus toxin binds to certain gangliosides present on neuronal cells, and some studies indicate that these gangliosides may act as the cellular receptor for tetanus toxin. It has also been proposed that tetanus toxin must interact with gangliosides plus an additional receptor in order for intoxication to proceed.

A vaccine based on the tetanus toxin, referred to as tetanus toxoid, causes the individual to produce antitoxin antibodies and thus provides active immunity. Survival of the patient after an active injection of tetanus does not cause immunity to further episodes of tetanus because the amount of neurotoxin sufficient to cause the disease is less than the amount of neurotoxin necessary to produce active immunity.

Anti-tetanus toxin immunoglobulins derived from humans are available to produce passive immunity. Equine tetanus antitoxin is also available, but it is less favored because of a shorter half-life and greater problems with hypersensitivity and serum sickness as compared to the human immunoglobulin.

Active immunization against tetanus, as well a number of other diseases, is routinely recommended for all members of the population. Typical immunization schedules begin with infants. The usual recommendation is four doses of tetanus toxoid vaccine by about 18 months of age with a fifth dose before entering school at about age 4 or 5. Normally, the vaccination is repeated about every 5 to 10 years thereafter depending on the individual's exposure to tetanus.

The current tetanus vaccine licensed for human and veterinary use consists of tetanus toxin which has been chemically inactivated and partially purified. Typically, the toxin is treated with formaldehyde, but alternatively it may be treated with glutaraldehyde to become atoxic. This product produces long lasting immunity, but is poorly characterized and contains impurities which can cause adverse side effects. Although the toxin itself is innocuous when it has been treated in a form suitable for use in a vaccine, contaminants or other components of the vaccine may cause adverse reactions. Because the neurotoxin is purified from lysed *Clostridium tetani* cells, the process is time-consuming and involves some risk due to the production of the bacterial cultures which include a potent toxin.

Contaminants either from the lysed cells or from the procedure used to make the toxin atoxic can cause vaccination reactions in the individual patient. Furthermore, the conventional tetanus vaccines must be kept under refrigeration. This causes difficulties in transportation and storage which may be significant problems in underdeveloped regions where the vaccine may be most desperately needed. Recently, in the U.S., the overall death rate for tetanus was about 30%. Improved immunization status of the population can help decrease this mortality.

Tetanus toxin has 1315 amino acids and is synthesized by *C. tetani* as a single polypeptide chain that is proteolyzed to yield two fragments, the light chain (LC) derived from the amino terminus, and the heavy chain (HC) derived from the carboxyl terminus. The heavy chain has a molecular weight of about 100,000 and the light chain of about 50,000. The two chains are linked by a single disulfide bond and noncovalent interactions.

The heavy chain can be readily proteolyzed by papain and other proteases at one additional site resulting in formation of two fragments: the light chain linked by a disulfide bond to approximately one-half of the heavy chain (L-HC$_n$) including the amino terminal, and the carboxyl terminal one-half of the heavy chain (H$_c$) or Fragment C. Each of the three fragments of tetanus toxin appears to represent a functional domain necessary for different steps in intoxication. The LC is responsible for intoxication of target cells, and the H$_{cn}$ fragment has been proposed to translocate tetanus toxin across membranes. The H$_c$ fragment, or Fragment C, is required for recognition of and binding to target cells. This fragment also retains the ability of intact tetanus toxin to undergo retrograde axonal transport.

SUMMARY OF THE INVENTION

The invention provides an immunogen against tetanus toxin comprising a peptide including linear tetanus-toxin-specific epitopes. These linear epitopes are derived from the carboxy terminus portion of the heavy chain C fragment of the toxin. The immunogen is competent to induce a protective immune response to the toxin in a mammal. In a preferred embodiment, the epitope is defined by the amino acid sequence DKILGCDWYFVPTDEGWTND (Seq. I.D. No. 1). A cysteine can be optionally incorporated at the amino terminus for conjugation to a carrier protein.

The immunogen is preferably formulated into a vaccine adapted for administration to a mammal, especially a human. The peptide may be conjugated to a carrier protein suitable for use in a vaccine. Although the peptide is preferably produced by chemical synthesis, it could be produced by other means, such as recombinant techniques.

Preferred peptides are provided, but the invention is not so limited. Substantially equivalent peptides are included within the scope of the invention. An example of a substantially equivalent peptide is one which is capable of binding to an antibody raised against Seq. I.D. No. 1 and which comprises neither nonlinear epitopes of the tetanus toxin nor epitopes which are tetanus-toxin-specific but not recognized by antisera raised against Seq. I.D. No. 1. Another example is a peptide which induces an antibody competent to bind to the peptide described above and which comprises an antigenic single linear tetanus-toxin-specific epitope derived from the heavy chain C fragment of the toxin, but which does not induce an antibody which recognizes a conformational epitope on the tetanus toxin.

Additionally, the invention includes a first peptide competent to bind to an antibody induced by a second peptide having Seq. I.D. No. 1, wherein the first peptide is not recognized by antibodies which recognize conformational epitopes of tetanus neurotoxin.

The invention also provides a variety of antibodies. An example is an antibody competent to bind to a peptide comprising a linear, immunogenic, single tetanus-toxin-specific epitope derived from the heavy chain C fragment of the toxin but which does not induce an antibody which recognizes a conformational epitope on the tetanus toxin. "Immunogenic" in this context means that the peptide is competent to induce a protective immune response to the toxin in a mammal. An example of such a peptide is Seq. I.D. No. 1. An antibody of the invention may be formulated into a therapeutic suitable for administration to a mammal, preferably a human. The antibody may be produced by a variety of procedures including monoclonal techniques.

Methods of vaccination are also provided. A preferred method includes selecting an immunogen as defined above. The epitope is derived from the heavy chain C fragment of the toxin. The immunogen is competent to induce a protective immune response to the toxin in a mammal to which the immunogen has been administered. The method further includes administering an effective amount of the immunogen to the animal. The peptide of the selected immunogen preferably includes Seq. I.D. No. 1. The vaccine may be administered parenterally, usually subcutaneously or intramuscularly. Additionally, the vaccine can be adapted for oral administration. In such a case, the immunogen of the invention could be a component of a recombinant vaccine.

DESCRIPTION OF THE PREFERRED EMBODIMENT

Figure 1:
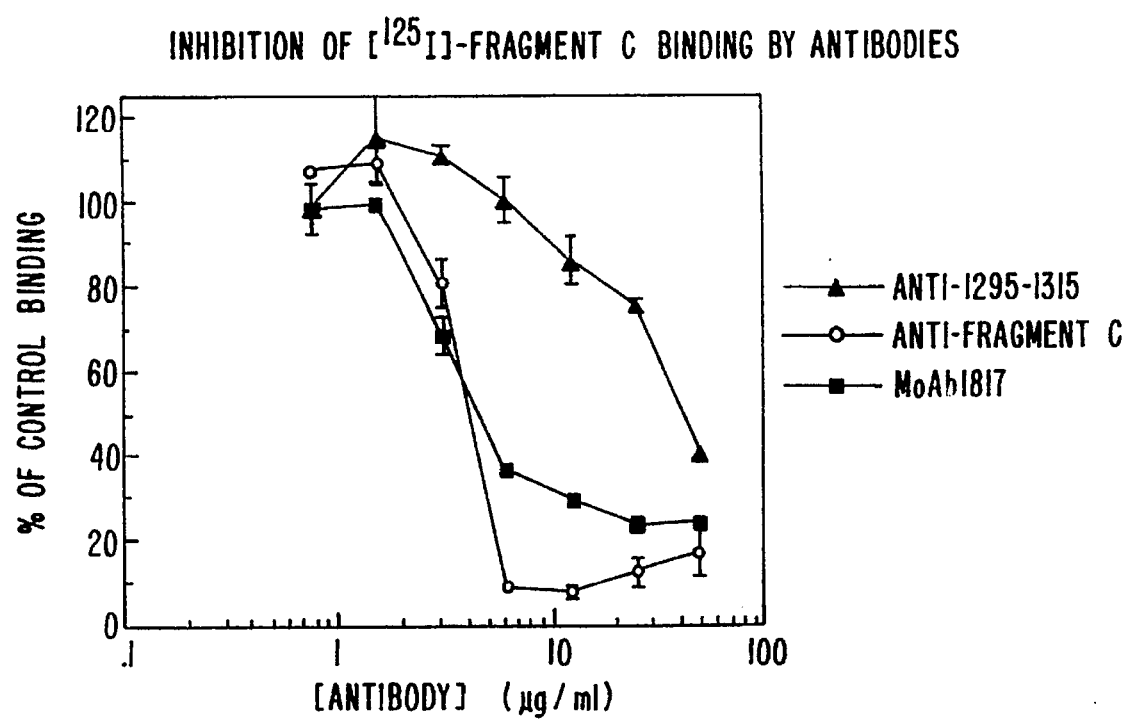
FIG. 1 shows inhibition of labelled Fragment C binding by several antibodies.

A preferred embodiment provides an immunogen including a 20 amino acid peptide derived from tetanus toxin which, preferably conjugated to a carrier protein, induces protective immunity against tetanus toxin. This peptide has potential use as a tetanus vaccine or vaccine component.

The peptides of the invention are significantly different from previous tetanus vaccines because they are well characterized molecules which are preferably chemically synthesized. Unlike the vaccines in present use, these peptides have potential use in recombinant vaccine vehicles, such as live oral vaccines.

A preferred peptide represents the final 20 carboxyl terminal amino acids of tetanus toxin and has the following amino acid sequence:

DKILGCDWYFVPTDEGWTND designated Seq. I.D. No. 1. Typically the peptide is conjugated to a cysteine at the amino terminus to facilitate conjugation to a hapten or carrier molecule such has a protein. Thus, another preferred peptide is represented by the following amino acid sequence:

CDKILGCDWYFVPTDEGWTND designated Seq. I.D. No. 2.

The linear epitope(s) of the present invention is Seq. I.D. No. 1. It can be presented to an immune system in a variety of known forms, some which are described below. The immunogen of this invention is directed to those having the epitope of Seq. I.D. No. 1 but not in combination with other native epitopes of the tetanus neurotoxin, especially conformational epitopes.

To identify the immunogens of this invention, one raises polyclonal antibodies specific to the tetanus neurotoxin or purchases appropriate antisera from Miles Inc., Lederle Laboratories, Baxter Healthcare Corp. The antisera is absorbed with an excess of BSA conjugated to Seq. I.D. No. 1. Conjugation is done according to *Proc. Natl. Acad. Sci.* 78:3403–3407 (1981).

The absorbed sera is thus used to test the capacity of the immunogens of this invention. Immunogens of this invention will not react with the crossreacted sera. Alternatively, one can use competitive immunoassays to establish whether immunogens carry native neurotoxin epitopes other than those of Seq. I.D. No. 1. A polyclonal antisera is raised against Seq. I.D. No. 1. A second peptide representing a linear sequence of tetanus toxin, which does not comprise a nonlinear epitope of tetanus toxin, that inhibits the binding of this antisera to Seq. I.D. No. 1 in an ELISA or immunoprecipitation reaction is an immunogen of this invention.

The peptides of the invention can be synthesized in solid or liquid phase as is known in the art. The peptide can be synthesized at different substitution levels. The synthesis may follow a stepwise format or a coupling approach. The stepwise method includes condensing an amino acid to the terminal amino group sequentially and individually. The coupling, or segment condensation, approach involves coupling fragments divided into several groups to the terminal amino acid. Synthetic methods include azide, chloride, acid anhydride, mixed anhydride, active ester, Woodward reagent K, and carbodiimidazole processes as well as oxidation-reduction and other processes. These processes apply to both solid and liquid phase synthesis.

Preferably the peptides are synthesized in the solid phase using a commercial polyacrylamide resin as an insoluble carrier. Usually the C terminal amino acid is bound to the insoluble carrier at its carboxyl group. Examples of such insoluble carriers include halo-genomethyl resins such as chloromethyl-polystyrene-divinylbenezene polymer, bromomethyl resin, hydroxymethyl resins, phenol resins, tert-alkyloxy carbonylhydrazidated resins, and crosslinked poly-N-acrylylpyrrolidine resins or other equivalent resin supports.

The reactive functional groups in the amino acid side chains are protected using protector groups known in the art. Some examples are the trifluoro-acetyl group, the fluorenyl-methoxycarbonyl group (Fmoc), butyl-ether and butyl-ester. The protected amino acids are activated individually with symmetrical anhydrides or esters such as those of pentafluorophenol and p-nitrophenol or any other side-chain protective group. A preferred system includes a polyamide resin or acidic resin and fluorenyl-methoxycarbonyl or tert-butyloxycarbonyl (Boc) as an α-amino group protector (the Fmoc-polyamide system) or equivalent system.

The peptide is removed from the resin, generally using an aqueous solution of trifluoroacetic acid (TFA) at room temperature (about 20°–25° C.) for sufficient time to remove certain of the protector groups, such as the butyl-ether and butyl-ester, but not the trifluoro-acetyl group. TFA is used for Fmoc synthesis, hydrofluoric acid (HF) or trifloromethone sulfonic acid (TFMSA) or an equivalent is used for Boc. This step also removes remaining protective group. This results in peptides in which the N-terminal group is available for conjugation with a hapten or carrier molecule.

The peptides are usually purified by a method such as gel filtration chromatography or high pressure liquid chromatography. For more information about peptide synthesis, see generally Stewart & Young, *Solid Phase Peptide Synthesis*, Pierce Chemical Company, Rockford, Ill. (1984). The above description is illustrative of current methods of peptide synthesis, but these methods are constantly changing. Other means of peptide synthesis would be applicable to synthesis of peptides of the invention.

There are a number of strategies for amplifying an immunogen's effectiveness, particularly as related to the art of vaccines. For example, cyclization or circularization of a peptide can increase the peptide's antigenic and immunogenic potency. See U.S. Pat. No. 5,001,049 which is incorporated by reference herein.

More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques" Bioconjugate Chem. 1:2–12 (1990).

The immunogen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of immunogen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the immunogen can range from about 5 µg to about 100 µg protein per patient. A preferable range is from about 20 µg to about 40 µg per dose. A suitable dose size is about 0.5 ml. Accordingly, a dose for intramuscular injection, for example, would comprise 0.5 ml containing 20 µg of immunogen in admixture with 0.5% aluminum hydroxide.

Conveniently, the vaccines are formulated to contain a final concentration of immunogen in the range of from 0.2 to 200 µg/ml, preferably 5 to 50 µg/ml, most preferably 15 µg/ml. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. The treatment may consist of a single dose of vaccine or a plurality of doses over a period of time. The immunogen of the invention can be combined with appropriate doses of compounds including other epitopes of the tetanus toxin. Also, the immunogen could be a component of a recombinant vaccine which could be adaptable for oral administration.

Vaccines of the invention may be combined with other vaccines for other diseases to produce multivalent vaccines. A pharmaceutically effective amount of the immunogen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is simple and routine to alter a natural protein's primary structure to create derivatives embracing epitopes that are identical to or substantially the same as (immunologically equivalent) the naturally occurring epitopes. Such derivatives may include peptide fragments, amino acid substitutions, amino acid deletions and amino acid additions within the natural amino acid sequence for the neurotoxin. For example, it is known in the protein art that certain amino acid residues can be substituted with amino acids of similar size and polarity without an undue effect upon the biological activity of the protein.

The following examples are for illustration only and are not intended to limit the invention in any way.

EXAMPLES

Example 1

Synthesis of peptide and KLH-conjugation

The published sequence of tetanus toxin (Eisel et al., EMBO Journal [1986] 5:2495–2502) was used to design a peptide with the sequence DKILGCDWYFVPTDEGWTND. The peptide was synthesized on a Applied Biosystems 430A peptide synthesizer according to the manufacturer's instructions. This peptide corresponds to the carboxyl terminal 20 amino acids of tetanus toxin (amino acid residues 1219–1315 of the toxin and residues 438–458 of $H_c$) prepared in vitro. A cysteine was incorporated at the amino terminus for conjugation to a carrier protein.

After synthesis, the peptide was conjugated to Keyhole limpet hemocyanin (KLH) using the cross-linker m-maleimidobenzoyl-N-hydroxysulfosuccinimide ester (Sulfo-MBS). Conjugation was performed by dissolving the KLH (10 mg) in 1 ml of 0.1M $NaH_cO_3$, and adding this solution to a vial containing 5 mg of Sulfo-MBS. The mixture was reacted at room temperature for 15 minutes, and then added to a second vial containing 10 mg of the peptide. This mixture was stirred at room temperature for three hours, dialyzed against 0.5% acetic acid overnight, and lyophilized.

Example 2

Anti-peptide-KLH production

The peptide-KLH conjugate was used to immunize rabbits by dissolving about 1 mg total protein in 1 ml of physiological saline, and emulsifying this with 1 ml of complete Freund's adjuvant. This mixture was injected into a rabbit at 4 subcutaneous sites. The rabbit was boosted with the same amount of peptide emulsified with incomplete Freund's adjuvant eight weeks later. Three weeks after boosting, approximately 25 ml of sera were collected from the rabbit via the ear vein.

Antibodies reactive with tetanus toxin were affinity purified by passing the sera over a tetanus toxoid-Sepharose affinity column constructed with tetanus toxoid and CNBr-activated Sepharose 4B (Pharmacia-LKB) according to the instructions of the manufacturer. Approximately 2.5 mg of tetanus toxoid was used per ml of activated gel.

The affinity-purified antibodies were tested for tetanus toxin neutralizing potency in the mouse neutralization assay. The purified antibody was found to have a potency of 6.4 U/mg protein.

Example 3

Synthesis of peptide and BSA-conjunction

A peptide corresponding to amino acids 1219–1315 of tetanus toxin was synthesized as described in Example 1 and coupled to bovine serum albumin (BSA) as described in Example 1 for KLH conjugation.

A cysteine was incorporated at the amino terminus for conjugation to a carrier protein. The peptide-BSA conjugate was prepared by dissolving 10 mg of bovine serum albumin (BSA) in 1.0 ml of 0.1M $NaH_cO_3$, pH 8.0, and transferring this mixture to a vial containing 5 mg of m-Maleimidobenzoyl-N-hydroxy sulfosuccinimide ester (Sulfo-MBS, Pierce, Rockford, Ill.). This mixture was incubated at room temperature for 15 minutes, 10 mg of peptide were added, and the incubation continued, with stirring, for an additional 3 hours. The conjugate was dialyzed against PBS, and stored at $-20°$ C.

Example 4

Anti-peptide-BSA antibody production

A rabbit was immunized subcutaneously with ~100 μg of peptide-BSA conjugate in complete Freund's adjuvant and boosted 3 and 6 weeks later with the same quantity in incomplete Freund's adjuvant. The rabbit was bled three weeks after the second boost, and antibodies specific for the immunizing peptide were purified by passing the serum over an affinity column as described in Example 2.

Example 5

Anti-peptide antibody characterization

A polyclonal antibody against the $H_c$ fragment was produced and purified using methods similar to Example 4. Monoclonal antibody 18.1.7 (MoAb 1817), which inhibits the binding of tetanus toxin and $H_c$ to gangliosides and neuronal cells, was produced as described by Kenimer, J. G., et al., "Monoclonal antibodies as probes of tetanus toxin structure and function", *Infect. Immun.* 42:942–948 (1983).

An antibody was raised against the synthetic peptide corresponding to amino acids 1295–1315 (anti-1295–1315) of the tetanus toxin to help determine if this region interacts directly with ganglioside. Ganglioside GT1b was purchased from Matreya, Inc. (Pleasant Gap, Pa.). Fragment C was purchased from Calbiochem-Behring, La Jolla, Calif. Anti-1295–1315 inhibited the binding of $[^{125}I]$-$H_c$ fragment to ganglioside coated microtiter plates in a concentration-dependent manner (FIG. 1). Both polyclonal antisera and a monoclonal antibody against $H_c n$ fragment also inhibited binding.

Anti-1295–1315 also blocked the lethal effect of tetanus toxin in a mouse protection assay. In this assay, the anti-peptide antibody had a potency of ~6.4 U mg purified antibody. In the same assay, a polyclonal antibody against $H_c$ purified by similar techniques had a potency of ~20 U/mg purified antibody.

Anti-1295–1315 inhibited the binding of $[^{125}I]$-Fragment C to gangliosides in a concentration-dependent manner. These data suggest that the carboxy terminal region of tetanus toxin is required for receptor recognition, either as a component of the ganglioside recognition site or as a domain necessary for retention of a functional confirmation.

---

What is claimed is:

1. A peptide comprising a linear tetanus-toxin-specific epitope, wherein said epitope is defined by the amino acid sequence of SEQ ID NO:1 and said peptide does not comprise additional epitopes of the native tetanus toxin.

2. A peptide of claim 1 which comprises a cysteine residue at the amino terminus (of SEQ ID NO:1).

3. An immunogenic composition comprising the peptide of claim 1 and a carrier molecule.

4. A method for manufacturing an immunogenic composition that elicits an immune response against tetanus toxin, comprising the steps of:

(a) selecting a peptide comprising a linear tetanus-toxin-specific epitope, wherein said epitope is defined by the amino acid sequence of SEQ ID NO:1 and said peptide does not comprise additional epitopes of the native tetanus toxin; and (b) formulating said peptide with a carrier molecule and pharmaceutically acceptable excipients.

5. The method of claim 4 wherein the peptide further comprises a cysteine residue at the amino terminus (of SEQ ID NO:1).

6. A method of eliciting in a human an immune response against a tetanus toxin, comprising the steps of:

(a) providing an immunogenic composition comprising a peptide comprising a linear tetanus-toxin-specific epitope, wherein said epitope is defined by the amino acid sequence of SEQ ID NO:1 and said peptide does not comprise additional epitopes of the native tetanus toxin; and (b) administering to a human an amount of the immunogenic composition effective to elicit an immune response against the tetanus toxin.

7. The method of claim 6 wherein the peptide comprises a cysteine residue at the amino terminus (of SEQ ID NO:1).

8. The method of claim 6 wherein the peptide is chemically synthesized.

9. The method of claim 6 wherein the administration is parenteral.

\* \* \* \* \*